United States Patent [19]

Hlynsky

[11] 4,083,851

[45] Apr. 11, 1978

[54] CIS-2,5-DIALKYLPYRROLIDINE PROCESS

[75] Inventor: Alex Hlynsky, Mentor, Ohio

[73] Assignee: Diamond Shamrock Corporation, Cleveland, Ohio

[21] Appl. No.: 587,223

[22] Filed: Jun. 16, 1975

Related U.S. Application Data

[63] Continuation-in-part of Ser. No. 431,067, Jan. 7, 1974, abandoned, which is a continuation-in-part of Ser. No. 253,550, May 15, 1972, abandoned.

[51] Int. Cl.$^2$ .......................................... C07D 207/06
[52] U.S. Cl. .................................. 260/326.8; 260/690
[58] Field of Search ............................. 260/326.8, 690

[56] References Cited

U.S. PATENT DOCUMENTS

| 3,177,258 | 4/1965 | Rylander et al. | 260/326.8 |
| 3,890,329 | 6/1975 | Benezra | 260/326.8 |

OTHER PUBLICATIONS

Ponomarev et al.; Chem. Abs. vol. 65, col. 2219c (1966).
Overberger et al.; J.A.C.S. 77, pp. 4100–4102 (1955).
Stiles; Chem. Abs. vol. 65: 82n (1966).
Chegolya et al.; Chem. Abs. vol. 69: 70178n (1968).

*Primary Examiner*—Donald G. Daus
*Assistant Examiner*—Mary Vaughn
*Attorney, Agent, or Firm*—Helen P. Brush

[57] ABSTRACT

A cis-2,5-dialkylpyrrolidine is produced from 2,5-dialkylpyrrole or 2,5-dialkyl-1-pyrroline by an improved hydrogenation process using a ruthenium metal catalyst on an alumina or titania support.

10 Claims, No Drawings

CIS-2,5-DIALKYLPYRROLIDINE PROCESS

BACKGROUND OF THE DISCLOSURE

This application is a continuation-in-part of my co-pending application, Ser. No. 431,067, filed Jan. 7, 1974, and now abandoned, which application is, in turn, a continuation-in-part of application Ser. No. 253,550, filed May 15, 1972, now abandoned.

This invention relates to an improved process for producing cis-2,5-dialkylpyrrolidines. More particularly, the invention provides an improved hydrogenation process employing a supported ruthenium catalyst.

Evans in JACS, 73, 5231 (1951) reports that cis-2,5-dimethylpyrrolidine can be prepared by the catalytic reduction of 2,5-dimethylpyrrole at a hydrogenation pressure of about 45 psig using Adams (platinic oxide) catalyst in glacial acetic acid. Later, Overberger et al JACS, 77, 4102 (1955) report that cis-2,5-dimethylpyrrolidine can be prepared by catalytic reduction of 2,5-dimethylpyrrole at a hydrogen pressure of 40 psig using a 5% rhodium on alumina catalyst in glacial acetic acid.

U.S. Pat. No. 2,675,390, (Rosenblatt) issued Apr. 13, 1954, describes the hydrogenation of pyrrole using a 5% rhodium on alumina catalyst in solvents such as glacial acetic acid and water. U.S. Pat. No. 3,177,258, (Rylander et al) issued Apr. 6, 1965, suggests hydrogenation of pyrroles using a catalyst containing ruthenium combined with another platinum group metal. Further, A. A. Ponomarev et al, in Khim. Geterotsikl, Soedin., Akad. Nauk. Latv. SSR, 239–42 (1966), report the hydrogenation of pyrrole to pyrrolidine at a pressure of 105 atm and 100° C, using a ruthenium catalyst on a silica support.

None of these procedures has proved satisfactory for the commercial hydrogenation of a 2,5-dialkylpyrrole. Separation of the alkaline product from a solvent such as acetic acid is difficult and time consuming. There is loss in yield because the pyrroles polymerize in acetic media with a subsequent waste disposal problem. Platinum and rhodium catalysts are quite expensive. The combination of ruthenium with another platinum metal requires costly steps in recovery of each of these metals from the spent catalyst. Ruthenium on a silica support is not an effective catalyst. There is a definite need for a process which employs catalysts and/or solvents which are easier to handle, do not create a pollution problem and are less costly.

SUMMARY OF THE INVENTION

This invention provides an improved process for catalytic hydrogenation of 2,5-dialkylpyrroles and 2,5-dialkyl-1-pyrrolines to cis-2,5-dialkylpyrrolidines. The process employs an improved heterogeneous supported ruthenium catalyst at reaction temperatures of 55°–180° C and at hydrogen pressures of about 15 to about 1500 psig. Water or, if desired, cyclohexane may be used as the solvent medium. The process provides cis-2,5-dialkylpyrrolidines having cis-isomer contents from about 80% to 100%.

DESCRIPTION OF THE PREFERRED EMBODIMENTS

The catalyst of this invention contains catalytically active ruthenium in the form of ruthenium metal on a support which is either alumina or titania. This catalyst can be prepared by applying the ruthenium compound in solution to the catalyst support, drying the treated support and then activating the ruthenium compound by reducing the dried support in a hydrogen gas stream at 400° C or higher, as described in U.S. Pat. No. 3,177,258.

The supported catalyst may contain from about 0.1% to about 10% by weight of catalytically active ruthenium based on total catalyst weight. In commercial practice, a particularly useful catalyst contains 5% ruthenium metal on a powdered alumina support.

Anhydrous 2,5-dialkylpyrroles and 2,5-dialkyl-1-pyrrolines may be used. If desired, a solution of the pyrrole dissolved in an inert solvent such as water of cyclohexane which is not reactive either with 2,5-dialkylpyrroles, 2,5-dialkyl-1-pyrrolines or cis-2,5-dialkylpyrrolidines, may be used. Generally, from about 20% to about 1% of the supported catalyst may be employed by weight of the dialkylpyrrole.

As described previously, hydrogenation pressure may vary generally from about 15 to about 1500 psig. However, it is preferred to conduct the reaction at hydrogen pressures of 300–500 psig from the standpoint of ease of operation, safety and economy. Likewise, the reaction may be conducted generally at a temperature ranging from 55° C up to and including 180° C, the higher the temperature, the faster the reaction. However, selectivity is sacrificed at the highest reaction temperatures. Accordingly, for optimum yields of the desired cis-products within commercially feasible reaction times, the reaction preferably is conducted at 120°–150° C. The total hydrogenation time generally may vary from about 2 hours to about 24 hours. In preferred embodiments of the invention, the process may be completed in 2–10 hours.

After hydrogenation is complete, the catalyst is separated from the hydrogenation mixture and the mixture analyzed by vapor phase chromatography using an Amine 220 column (Supelco, Inc., Bellefonte, Pa.) to determine percentage conversion and cis-isomer content. Cis-isomer contents of the pyrrolidine may vary from about 85% to about 95% ± about 5%. Results of the vapor phase chromatography analyses are cross checked by NMR analysis of the phenyl urea derivatives. When water is used as a solvent, the product, such as dimethylpyrrolidine, is soluble in water and forms an azeotrope on distillation. To reduce water content, the pyrrolidine-water azeotrope is distilled first. At atmospheric pressure, this azeotrope distills at 87°–89° C and contains about 33% water, by weight. When anhydrous pyrrolidine is desired, the pyrrolidine-water azeotrope is first distilled in the presence of benzene; the benzene-water azeotrope distills first leaving the anhydrous 2,5-dimethylpyrrolidine isomer mixture behind.

For a fuller understanding of the nature and objects of this invention, reference may be made to the following examples. These examples are given merely to illustrate the invention and are not to be construed in a limiting sense. All are by weight unless otherwise indicated.

EXAMPLES 1-12

Using a stirred, stainless steel autoclave, 2,5-dimethylpyrrole is hydrogenated using the quantities of pyrrole, catalysts and solvents at the reaction conditions shown for each example in the table. The catalysts used have been obtained commercially or have been prepared according to the procedure described in U.S. Pat. No. 3,177,258 in which a ruthenium compound in solution is deposited on the support, the treated support is dried and the ruthenium is activated by reducing the dried support in a hydrogen gas stream at 400° C.

In carrying out the hydrogenation, catalyst, pyrrole and solvent, if used, are charged into the reactor. The reactor is then purged several times with nitrogen to remove air, and then pressure tested with nitrogen at room temperature. If the pressure test is satisfactory, the reactor is purged and charged with hydrogen. The reactor is then heated to the desired temperature and the hydrogen pressure adjusted to the desired pressure. Hydrogen pressure is maintained at the desired level until the hydrogenation is complete, that is, until no additional hydrogen is consumed.

After hydrogenation is complete, the reactor is cooled to below 50° C and hydrogen vented. The hydrogenation reaction mixture is removed and allowed to settle. The product mixture is then separated from the solid catalyst by decanting the supernatant liquid.

The product mixture is then analyzed by vapor phase chromatography. The chromatograph contains a 3/16 inch × 6 feet column packed with 5% Amine 220 on Chromosorb "G" High Performance (80-100 mesh) and is operated under the following conditions. The column is used at a temperature of 70°-90° for the quantitative analysis of cis- and trans-2,5-dimethylpyrrolidine and at a temperature of 150°-160° C for quantitative analysis of 2,5-dimethylpyrrole. The cis-isomer elutes first and is followed shortly by the trans-isomer after which the column temperature is immediately raised to 150°-160° C. The pyrrole elutes about 3 minutes after the pyrrolidine isomers under these conditions. From the amount of pyrrole left, the % of conversion is determined. Results of these analyses are shown in the table.

benzene following the procedure of Evans in JACS 73, 5231 (1951). Infared analysis of this urea showed the NH band at 3.1$\mu$, the $CH_3$ group at 3.5$\mu$, and the carbonyl band at 6.15$\mu$. The urea melts at 99°-101° C. Calc'd for $C_{14}H_{20}N_2O_1$: N, 12.1; Found: N, 12.1.

EXAMPLE 14

A 250 cc stainless steel stirred autoclave is charged with 5.0 g (0.051 M) of 2,5-dimethyl-1-pyrroline [Evans, JACS 73, 5231 (1951)], 0.1 g (2% by weight) of 5% ruthenium on alumina catalyst and 50 cc water. The reactor is purged with nitrogen twice and then with hydrogen and then pressure tested with hydrogen at ambient temperature. The reactor is then heated to 132° C at a pressure of 520 psig and these conditions are maintained for 2.5 hr until there is no further hydrogen uptake. The reactor is cooled to room temperature and the hydrogen is vented. After the mixture is removed from the autoclave, the catalyst is separated by filtration with the resulting filtrate analyzed by vapor phase chromatography. A 95% conversion is obtained with the product containing 85% of the cis-isomer of 2,5-dimethylpyrrolidine.

If a higher cis-isomer content is desired, the reduction mixture is fractionally distilled. For example, a 99+% cis-isomer may be obtained by distillation of a 92% cis-isomer product through a 50 plate Oldershaw Column at a 40:1 reflux ratio.

I claim:

1. A process for hydrogenating a heterocyclic compound selected from the group consisting of 2,5-dimethylpyrrole, 2-ethyl-5-methylpyrrole and 1,5-dimethyl-1-pyrroline to the corresponding dialkylpyrrolidine

| HYDROGENATION OF 44 G OF FRESHLY DISTILLED DIMETHYLPYRROLE | | | | | | | |
|---|---|---|---|---|---|---|---|
| | | Reaction Conditions | | | | Dimethyl Pyrrolidine | |
| Example No. | Catalyst (wt %) | Solvent (ml) | Temp. ° C | Press. psig | Time hr. | % Conversion | % Cis-isomer |
| 1 | 7% of 5% Ru on Alumina | 50 Water | 55 | 1400 | 22.50 | 98+ | 93.3 |
| 2 | 1% of 5% Ru on Alumina | 50 Water | 155 | 1400 | 4.25 | 98+ | 91.1 |
| 3 | 1% of 5% Ru on Alumina[1] | 50 Water | 150 | 1400 | 22.25 | 93 | 90.0 |
| 4 | 1% of 5% Ru on Alumina | 50 Water | 150 – 180 | 1400 – 1500 | 1.50 | 98+ | 83.4 |
| 5 | 1% of 5% Ru on Alumina | 50 Water | 130 | 500 | 7.00 | 98+ | 92.5 |
| 6 | 3% of 5% Ru on Alumina | 50 Water | 130 | 500 | 3.25 | 93 | 92.4 |
| 7 | 1% of 5% Ru on Alumina | 15 Water 35 Cyclohexane | 130 | 500 | 7.00 | 68 | 95.3 |
| 8 | 1% of 5% Ru on Alumina | 30 Water 20 Cyclohexane | 130 | 500 | 6.50 | 89 | 92.8 |
| 9 | 1% of 5% Ru on Alumina | 50 Cyclohexane | 150 | 500 – 800 | 7.25 | 61 | 94.2 |
| 10 | 3% of 1.5% Ru on Titania | 50 Water | 130 | 550 | 2.75 | 98+ | 89.0 |
| 11 | 3% of 1.5% Ru on Titania[2] | 50 Water | 130 | 550 | 2.25 | 92 | 92.3 |
| 12 | 3% of 1.5% Ru on Titania[3] | 50 Water | 130 | 500 | 7.50 | 97 | 90.5 |

[1] Repeat with catalyst from Example 2.
[2] Repeat with catalyst from Example 10.
[3] Repeat with catalyst from Example 11.

EXAMPLE 13

2-Ethyl-5-methylpyrrole is prepared according to the procedure of N. I. Shuikin et al, Izv. Akad. Nauk SSSR, Ser. Khim. 1965 (1). 163-5 (Russ), C. A. 62, 11759 (1965). This compound is hydrogenated to obtain cis-2-ethyl-5-methylpyrrolidine following the procedure given in Example 1 above. The product distills at 132° C at 760 mm and has a refractive index of 1.4330 at 24° C. Analysis by vapor phase chromatography shows that the product contains greater than 90% cis-isomer. Calc'd for $C_7H_{15}N$: N, 12.3; Found 12.0.

The phenyl urea derivative is prepared in 73% yield by reacting the pyrrolidine with phenyl isocyanate in predominantly as the cis-isomer, which process comprises contacting said heterocyclic compound at a temperature of 55°-180° C and under a hydrogen pressure of 15-1500 psig with ruthenium metal catalyst on a support which is either alumina or titania.

2. A process of claim 1 wherein the ruthenium content of the catalyst is from about 0.1% to about 10%, by weight.

3. The process of claim 1 wherein the heterocyclic compound is 2,5-dimethylpyrrole.

4. The process of claim 1 wherein the heterocyclic compound is 2,5-dimethyl-1-pyrroline.

5. The process of claim 1 wherein the supported catalyst concentration is from about 20% to about 1% by weight of the heterocyclic compound, said supported catalyst containing from about 0.1% to about 5% by weight of catalytically active ruthenium.

6. The process of claim 1 wherein the catalyst contains, by weight, 5% ruthenium on a powdered alumina support.

7. The process of claim 1 wherein the process is conducted in a solvent medium which is water or cyclohexane.

8. The process of claim 7 wherein the solvent medium is water.

9. The process of claim 1 which is conducted at a temperature of 130° C and under a hydrogen pressure of 500 psig.

10. The process of claim 1 wherein the ruthenium metal catalyst support is titania.